United States Patent [19]
Dechene et al.

[11] Patent Number: 5,448,172
[45] Date of Patent: * Sep. 5, 1995

[54] TRIBOELECTRIC INSTRUMENT WITH DC DRIFT COMPENSATION

[75] Inventors: Ronald L. Dechene, Boxford; Robert E. Newton, Tewksbury; Ron L. Swartzentruber, Somerville, all of Mass.

[73] Assignee: Auburn International, Inc., Danvers, Mass.

[*] Notice: The portion of the term of this patent subsequent to Feb. 15, 2011 has been disclaimed.

[21] Appl. No.: 57,611

[22] Filed: May 5, 1993

[51] Int. Cl.⁶ .............................................. G01N 27/60
[52] U.S. Cl. ..................................... 324/454; 324/71.1
[58] Field of Search ............... 324/454, 71.3, 71.1, 324/72.5, 72

[56] References Cited
U.S. PATENT DOCUMENTS 4,714,890  12/1987  Dechene et al. ................. 324/71.1
5,287,061   2/1994  Dechene et al. ................. 324/454

Primary Examiner—Walter E. Snow
Attorney, Agent, or Firm—Edwin H. Paul; Jerry Cohen

[57] ABSTRACT

A microprocessor (48) controlled triboelectric instrument with probe fouling detection, zero offset adjustments and temperature compensation. The system programmability provides for enhanced operator control and operator monitoring wherein the system may be reprogrammed to advantage to reduce instrument down time.

3 Claims, 2 Drawing Sheets

TRIBOELECTRIC INSTRUMENT WITH DC DRIFT COMPENSATION

CROSS REFERENCE TO RELATED APPLICATIONS

This application is closely related to U.S. Pat. Nos.: 4,904,944 issued on Feb. 27, 1990; 4,714,890 issued on Dec. 22, 1987; 4,619,145 issued on Oct. 28, 1986; 4,774,453 issued on Sept. 27, 1988; 4,631,482 issued on Dec. 23, 1986; and to U.S. application Ser. No. 07/885,493 filed May 19, 1992. These patents are of common assignment with this application, and the disclosures of all are hereby incorporated by reference, as though set out at length herein.

1. Field of the Invention

The present invention relates to instrumentation for measurement of flow and mass flow rates, and especially to electronic circuitry which connects directly to the physical measuring probe. This circuitry accepts the current signal from the probe through a conversion function made up of a variable gain two stage amplifier. The first stage has provisions for introducing a signal which compensates for DC drift within the system. The conversion output is fed to microprocessor section which controls the apparatus.

2. Background of the Invention

The measurement of gas with solid particles therein and certain fluids which behave similarly, is of importance in many industries, e.g. chemical processing, food handling, transport loading and unloading, filtration, aeronautics and combustion fuel feeds. The above referenced patents have provided significant improvements in this general technical field.

Current flow measuring systems electrically connect the triboelectric sensor probe through an ultra low noise cable. The signal connection is fed to a low impedance conversion circuit (converter). A conversion circuit will amplify the input signal, where for the purposes of this invention amplification is defined broadly as voltage amplification, current amplification, impedance amplification (impedance reduction) or combinations thereof. An over-voltage protector is installed at the probe, and a current limiting barrier resistor before the converter's summing junction provides intrinsic safety for the probe and cable allowing the probe to be installed in hazardous environments.

Electrical offsets and drifts are of concern in the various circuits, and arrangements disclosed in the above referenced patents are used to compensate for these offsets and drifts. Other circuit implementations known in the art may also be used. These techniques as embodied in the circuits provide several approaches to drift compensation. One technique disconnects the circuitry from the probe (and usually forces the output to some known position, often zero) measures and stores the output of the first stage, using that output to force the output to zero via feedback. The first stage is typically compensated since subsequent electronic stages have a drift effect which is diminished by a factor of the gain of the first stage. That is if the first stage has a gain of 1000, the drift of the second stage has only 1/1000 of the effect of the drift of the first stage, and so the second stage drift is often inconsequential. The compensation signal is held and functional as the circuitry is reconnected back to the probe. This sample and hold compensation technique may be done at given intervals or just before a measurement is to be taken. One limitation with this technique is that it compensates for the offset and temperature drift at a point in time—the sampling time, but drifts once the probe is reconnected to the circuitry will still be mistaken as signal. Other techniques use thermistors or the like to model the temperature drift characteristics of the first stage and thereby compensate for the temperature drift continuously. A limitation with this technique is that the thermistors or the like and compensation circuitry do not exactly track the electronics involved.

Another limitation of instrumentation, when practically applied in the above fields, to perform the measurement and feedback control of flow has been contamination of the physical probe. Any conductive substances, e.g. acids or other electrolytes, contained in the materials whose flow is being measured, may eventually build up providing electrical leakage paths which give rise to measurement errors. Also system errors occur as sensitivity (gain) and system zero change due to inexact temperature compensation, drift and/or other causes.

Old methods to solve this contamination problem have involved disassembly and cleaning or purging of the the probe on a routine basis, and system calibration or other external testing circuits are used to monitor or measure system gain and zero. Employing these methods involves taking the system off-line and having skilled technicians perform the work.

It is a primary object of this invention to provide an improved temperature compensation apparatus wherein the temperature drift of the electronics connecting to the probe is compensated such that substantially no temperature drift signal occurs.

It is an object of this invention to provide a means where the circuitry is efficiently changed such that different filtering and compensation techniques are quickly and easily installed.

Another object of this invention is to minimize system down time and make efficient use of a technician's time.

It is an object of this invention that probe-contamination, gain or zero change detection circuitry be included that does not unduly interfere with or otherwise compromise the efficacy of the triboelectric detection instrumentation.

SUMMARY OF THE INVENTION

The present invention provides an improved circuit which compensates for temperature drift continuously wherein there is essentially no temperature drift of the output signal. The present circuitry also provides a flexible means whereby the gain, temperature compensation, electronic filtering can be easily and efficiently modified. The present circuitry also provides for the detection of contamination between the probe and ground, system gain changes and system zero changes without degrading or otherwise compromising the triboelectric instrument usefulness or sensitivity, and without unduly taking the system off-line.

An uncontaminated probe appears as an open circuit to the circuitry that receives the signal from the probe. The mass flow physically interacts with the probe creating a signal (triboelectric effect)—the signal being charge either supplied to the probe or taken from the probe. Thus causing the signal to take the form of a small current. Compensation signals are fed into the receiving circuitry to counteract offsets and other drifts. In addition, an AC detection signal is fed into the converter and the resulting corresponding output signal from the converter is a measure of the voltage gain of the converter. If the voltage gain has not changed the probe is uncontaminated. Also, a circuit is implemented to allow determination that the system gain (independent of the probe contamination) and system zero are also acceptable.

The present system provides for a computer (microprocessor based in a preferred embodiment) means which has stored the temperature drift characteristics of a specific circuit. The system is calibrated, in a preferred embodiment of the present invention, by isolating the computer based circuitry from the process to be measured or monitored and changing the ambient temperature of the system over a known range. A temperature measuring device is provided which allows the computer to continuously measure the temperature of the first stage. As the temperature is changed, the correction required to return the signal to zero is measured and stored by the computer. A profile of the temperature of the circuitry is learned and stored as a look-up table. In later operation of measuring a process, the computer measures the temperature of the first stage and provides a correction signal based on the stored temperature data such that essentially no temperature signal appears at the output of the system.

In a preferred embodiment the probe is an open circuit, but when the probe is contaminated an electrical leakage path is established from the probe to the common signal return (ground). In this preferred embodiment the voltage gain of the converter is dependent upon the impedance of the probe to the signal return. The detection signal experiences a voltage gain due to the same circuit components as the probe signal experiences. When the probe impedance does not appear as an open circuit to the converter, the gain of the converter increases, and so a different level of the detection signal output is measured. This different level indicates a gain increase which in turn indicates that conductivity exists between the probe and signal return. Thus indicating contamination and need for cleaning. The actual indicator to an operator may be of any known type including, but not limited to, a light, message display, flag or transmission.

The detection signal must be distinguished from a signal emanating from the triboelectric effect. Many techniques, known in the art may be used to accomplish this separation. In one preferred embodiment an alternating (AC) signal is used whereby the signal is easily extracted, by synchronous filtering, or other means, in hardware or software, from the triboelectric signal without affecting the triboelectric signal. Hence there is no interaction between these signals and no degradation of the triboelectric instrument capabilities.

System zero is monitored by shunting the probe signal current directly to ground and disconnecting it from the converter input. With no input signal the converter output may be measured to ensure that the system is at "zero". The switch may be an electronic or electromechanical relay, as in one preferred embodiment, a switch, any electronic switch (FET, transistor, etc) or the like.

Attaining the necessary system sensitivity requires the use of very high impedance components (resistors, op-amps, etc) which sometimes malfunction. Switching means is used to isolate the probe and cable from the converter. The gain of the converter is then monitored to ensure acceptable gain. In addition, switch means may be used to select other resistors whereby the gain of the converter stage is checked including the high value resistors of the conversion section. Any fault is thereby related to the high value resistors or the other circuit components. These switch means are operated with the instrument on-line although the triboelectric measurement must be suspended for the short time of checking the system gain and zero.

Other objects, features, and advantages will be apparent from the following detailed description of preferred embodiments taken in conjunction with the accompanying drawing in which:

DETAILED DESCRIPTION OF PREFERRED EMBODIMENTS

Figure 1:
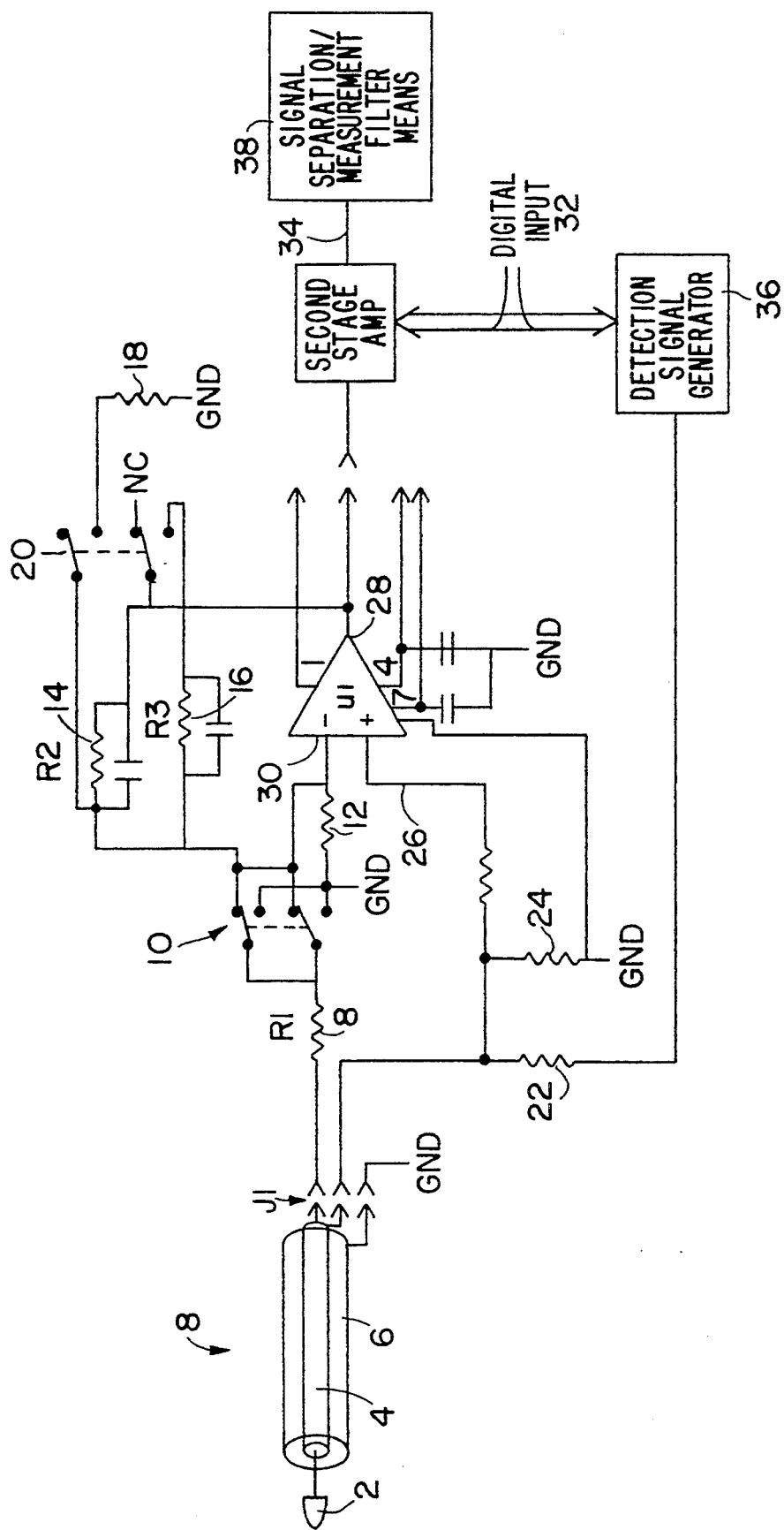
FIG. 1 is a circuit/block diagram of a preferred embodiment of the present invention.

FIG. 1 is a schematic/block diagram of a preferred embodiment of the present invention. In the on-line working configuration the latching relays K1 and K2, are activated as shown. R1 is connected to the inverting input 30 of an operational amplifier U1. Triboelectric signal charge is transferred to the probe 2, defining a signal current (the time rate of charge transfer). This signal current is transformed into a voltage at the output of the op-amp U1. U1 performs a current-to-voltage conversion (converter) of the signal current. In other embodiments a charge amplifier, a voltage amplifier, a current amplifier, an impedance transformer and combination thereof may be used. The converter input 30 is connected through resistor R7 to ground. Ground is herein defined as a signal return which may (but not necessarily) be 0 volts. The probe 2 is physically placed in the moving stream of material being measured, where charge per unit time (current) is transferred to the probe. That current is fed through the triaxial cable 8 to resistor R1. R1 is of a value which ensures that the the probe can never exceed the current specification requirement for intrinsically safe circuitry as defined by Underwriters Laboratories, Factory Mutual Research, or other like safety organizations.

Current flows through R1 and enters the inverting summing junction 30 of op amp U1, with the latching relay K2 activated as shown. An equal current leaves the summing (inverting) junction via R2. R7 is very large (typically twice the value of R2), providing a specific voltage gain for the gain test signal and workable voltage at the output 28 of U1. U1 has low leakage or bias current and drift characteristics consistent with the signals being measured. The non-inverting input to U1, 26, is connected through R6 and R4 to ground, and compensation and detection signals are introduced to input 26 of U1 through R5, as discussed below.

The description of the typical operation of the circuit to measure triboelectric signal current from the probe 2 follows. Small offsets, leakage currents and bias current are disregarded in the following discussion, but are routinely handled within the known art. Signal current runs through the triaxial cable 8 through R1 to the summing input 30 of U1. An equal current flows out from the summing junction through R2 due to the voltage output 28 of U1. Resistors R6 and R4 at the non-inverting input 26 of U1 are of a value that the voltage at 26 is at ground (discounting leakage and offsets). The operational amplifier U1 works to force the voltage at input 30 to be equal to the voltage at 26 and so input 30 is at ground and substantially no signal current flow through R7. The equivalent signal current flows through R2 creating a voltage drop across R2. This voltage drop is directly proportional to the signal current, and measurement of this voltage drop is a measure of the rate of charge picked up by the probe 2. Also, the integration of the voltage over time is a direct measure of the amount of charge picked up by the probe over the integration time.

Viewing the converter circuit from the input 26, with the relays activated as shown and the probe 2 an open circuit, the DC voltage gain from the input 26 to the output 28 is 1+(R2/R7). With a 5 G ($G = 1 \times 10^9$) ohm R2 and a 10 G ohm R7, this gain is 1.5. Introducing a known signal amplitude though R5 to input 26, and measuring the signal output at 28 the gain may be verified. If the gain is the expected 1.5 no service is indicated. But if the gain is not equal to 1.5 the probe may be contaminated, R7 and/or R2 may have drifted, or the op amp U1 and the supporting components may have malfunctioned. By activating K1 the probe signal is shunted to ground and is isolated from the converter circuitry, so that any contamination of the probe will not affect the gain of the converter. In this configuration if the gain is remeasured as 1.5, the probe is (most likely) contaminated and so requiring service. If the gain is not equal to 1.5, R2, R7 or U1 are most likely faulty. Activating K2 places much smaller resistors R3 and R8 in parallel with R2 and R7, respectively. In this preferred embodiment the ratio R3/R8 is the same as R7/R2—thus the same voltage gain is maintained, but the current to voltage conversion gain is decreased. Again by measuring the gain, the fault can be determined to be with the resistors R2 and/or R7 or with U1.

In this preferred embodiment the detection signal and the triboelectric signal are combined at the output of U1. The detection signal and the triboelectric signal must be separated from each other so neither interferes with the other. In this preferred embodiment the detection signal 36 is a frequency substantially entirely separated from the triboelectric signal by filter means 38, either in hardware or in software or a combination thereof. Other techniques of combining and separating (multiplexing/de-multiplexing) such signals together are well known in the art. In this embodiment the cable 8 may be long and contribute significant capacitance from the cable signal line to ground if it were a coaxial construction. The capacitance of a long cable would prohibit application of the AC detection signal to the signal line due to the long time constant formed by the capacitance and R1 and other circuit components. The cable 8 is a triaxial cable wherein the inner shield 4 is driven from the same AC detection signal which appears on the cable signal line (from the input 30 through R1 by operation of the operational amplifier U1), causing the same voltage to appear on the signal conductor and inner shield, cancelling the capacitance effect of the cable. The range of frequencies for the detection signal may be broad only limited by the frequency effects of the circuitry and the ability to substantially completely separate the detection and triboelectric signals.

In this preferred embodiment, probe fouling is detected by subtracting the average values of the two half cycle components, produced during alternate half cycles of the detection signal. The difference value which constitutes probe fouling is directly related to the square root of the second stage voltage gain.

The system zero is verified periodically. With K1 shunting the probe signal to ground and isolating the converter input, and with no other inputs, the output of the op-amp U1 should be substantially at ground potential(zero volts). If the output varies from ground then the microprocessor produces a correction signal via R5, R4 and R6 to U1 input 26 which brings the output 28 of U1 to zero volts. The difference between the correction signal and the temperature correction signal (in effect at the time) is retained and used to correct measurements until another zeroing sequence is initiated. If the output of op amp U1 varies substantially from ground (zero volts) a malfunction may have occurred and service is indicated.

The span (sensitivity) is verified following each zero verification. With K1 shunting the probe signal to ground and isolating the converter input the microprocessor produces a known voltage at U1 input 26 while setting the gain of the input stage via K2 to a known level. The voltage gain of the second stage amplifier is also set to a known level and the resulting signal represents the overall gain. Minimum and maximum gains of both stages are compared to insure proper operation over the entire gain range.

In practical applications the operation of the entire instrument will be verified as acceptable.

In summary, the verifications can be made without taking the instrument off-line, and if acceptable, no down time will be required. In addition faulty areas may be isolated from each other before taking the system off-line, and periodic checks of system zero and gain may be made without taking the system off-line and with substantially no impact on the instrument's throughput.

Figure 2:
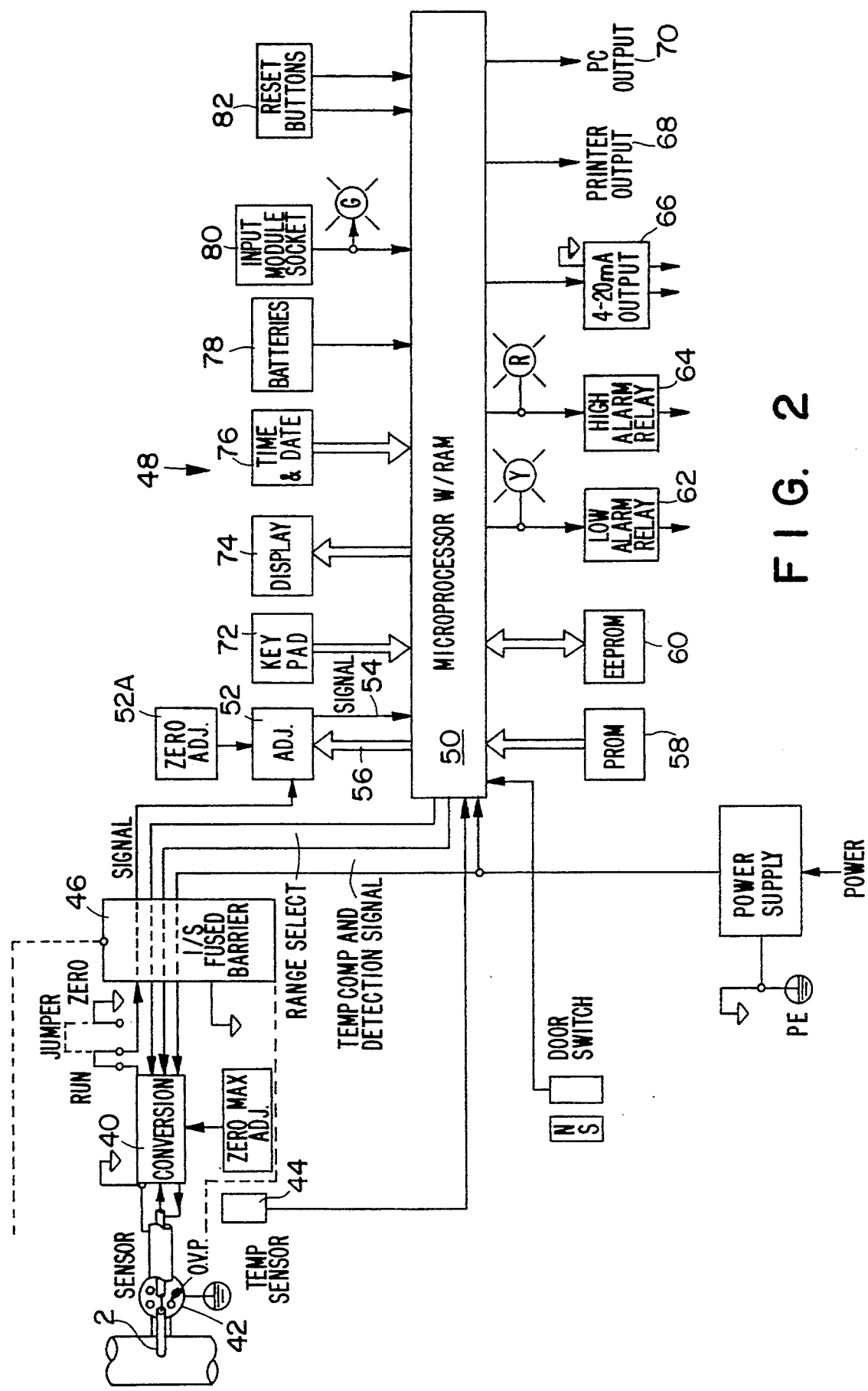
FIG. 2 is a system block diagram of a preferred embodiment of the invention.

FIG. 2 is a system block diagram of the instrument. The preceding discussion focused primarily on the conversion section 40. The probe 2 has adjacent over voltage protection (OVP) devices 42 to limit any voltage on the probe to a safe level should the cable become disconnected. The temperature sensor 44 shows the close proximity of the sensor to the first stage.

The conversion section connects to the microprocessor section 48 of the instrument via an intrinsic safety barrier interface 46. This interface comprises seven fused, redundant zener diode barriers which limit the available voltage at the input stage to no more than ±15 volts regardless of any foreign voltage which may be applied to the remainder of the circuit.

The microprocessor section 48 includes:

PROM 58—a programmable read only memory that stores the application program for the instrument.

Electrically erasable EEPROM 60 stores the temperature compensation and instrument set-up data.

High 64 and low 62 alarm relays provide the user with two levels of occurrences needing immediate attention. At most installations background (normal) emissions produce only a small output signal as compared to that produced by the maximum allowable emissions (compliance) levels. A low level alarm is generated when a dust emission level is higher than normal but not beyond compliance levels or when a system malfunction is detected. Typical malfunctions are low battery voltage, door open, signal loss (disconnected sensor), saturated signal (gain too high) and contaminated probe. A high level alarm is generated when a dust emission level exceeds the compliance level.

Analog output port 66 is provided to allow communication to other systems for monitoring or data logging.

Printer port 68 and PC port 70 are provided to allow serial data communication of peripheral devices. This communication may be a voltage or current transmission and is used for remote monitoring of system faults, emission warnings, real time emissions levels, as well as long term data retention.

Key pad 72 and display 74 assist the user in programming, operating and monitoring the system.

Calendar module 76 maintains real time and date for the system which allows for data logging and controls auto zero and span timing.

Battery 78 backs up the system so power failures will not destroy recorded data or maintenance of real time.

The EEPROM is not affected by power loss or battery failure and since system operating parameters are stored in the EEPROM the system will return to normal operation after a complete power loss with the exception of actual time displayed and the need to be reset.

Reset buttons 82 are provided, one resets the entire system, while the other allows access should the password be forgotten by the user. The input module socket 80 may be an on-off type to provide a timing input to determine the source of an abnormal emissions level in the case of applications where the triboelectric probe is fed by multiple emission sources, or sequentially cleaned filters, orit may be an analog type to allow the input of an external signal such as the gas velocity.

An open door detector reminds the operator to close the door after keypad activity has ceased for a short period of time to protect the system from damage.

Such a system provides for a flexibility allowing the user automatic operation and many other options. The system provides for reprogramming for bug-fixing and updating with minimal user down time. Such a system also provides for servicing the instrument from remote locations and for continuous logging of system status to assist in trouble shooting and monitoring the system.

The triboelectric signal from probe 2 is converted into usable means by the conversion block 40 which can also be referred to as the first conversion gain stage. The range of this gain stage is determined by the microprocessor via the range select line.

The converted triboelectric signal is fed through a gain adjust block 52, where a multiplying digital to analog converter is used to control the amount of second stage gain. This signal is then digitized and sent to the microprocessor 54 where filtering or various other operations can be performed on it before it is output to a display, readout or other means.

Due to amplifier inconsistencies, a manual zero adjustment is provided for both gain stages. This is performed for the second stage by block 52A and block (zero max adj.) for the first stage.

Along with the manual first stage conversion gain adjustment, the instrument has the ability to automatically control and periodically measure the zero and compensate for it. The instrument also has the ability to measure and compensate for ambient temperature variations detected by the temperature sensor 44. Both of these measurements are compensated for at the converter by the means of the Temp Comp and Detection Signal line.

It should be said here as well that the Temp Comp and Detection Signal line is also the line used by the microprocessor to create an AC signal, which is the means for determining Probe Fouling as described earlier.

It will now be apparent to those skilled in the art that other embodiments, improvements, details, and uses can be made consistent with the letter and spirit of the foregoing disclosure and within the scope of this patent, which is limited only by the following claims, construed in accordance with the patent law, including the doctrine of equivalents.

What is claimed is:

1. A triboelectric instrument comprising:
   (a) a probe;
   (b) a converter means, wherein a triboelectric signal is received from the probe and converted to an amplified signal,
   (b) a triaxial cable, with a center conductor, an inner shield, and an outer shield, connecting the probe to the converter,
   (c) means for adjusting zero offset of said triboelectric signal,
   (d) means for measuring and compensating for temperature drift of said instrument,
   (e) means for isolating said probe from said converter means, means for introducing an AC signal into the converter means, where said converter produces an AC output signal, and wherein a change in said AC signal output indicates a faulty circuit component,
   (f) means for grounding said signal and isolating said converter inputs wherein said converter output verifies an acceptable system zero, and
   (g) means to drive said triaxial inner shield rendering said cable capacitance ineffective in distorting, or otherwise altering said amplified signal,
   (h) processor means for controlling said instrument, wherein said temperature compensation and said zero offsets are measured, stored and controlled by said processor.

2. An improved triboelectric probe circuit comprising:
   (a) a converter means, wherein a triboelectric signal is received from a probe and converted to an amplified output signal,
   (b) means for introducing a detection signal into said converter wherein said detection signal is converted to an amplified output detection signal by utilizing substantially the same components as used to convert said triboelectric signal, wherein said amplification is dependent upon the degree of probe contamination,
   (c) means for measuring said amplified output second signal wherein a change in the value of said converted output signal indicates a contaminated probe,
   (d) a microprocessor for controlling the probe circuitry wherein the microprocessor has the ability to learn and remember the necessary amplifier corrections needed for variances in the ambient temperature and to correct for them in real time,
   (e) means for determining thresholds of probe contamination for all available gain values,
   (f) means for an operator unskilled in the art to enter setpoints for low and high emission alarms, alarm time delays, triboelectric signal time averaging for display of triboelectric signal, sensitivity, time and date, user defined password, user selection of the form of the analog output, time of the day for a routine Quality Assurance Report, and the means for the instrument to remember all of the above setpoints even in the case of power failure, (g) means for notifying operator of said setpoints, various alarms, triboelectric signal value, correlated emissions rate, and system self checks with the use of a display readout or other.

3. An instrument as defined in claim 1 further comprising: a filter for detecting and separating the AC signal from the triboelectric signal, wherein said filter comprises electronic circuitry and software.

* * * * *